United States Patent [19]

Kellems et al.

[11] Patent Number: 4,822,736
[45] Date of Patent: Apr. 18, 1989

[54] AMPLIFICATION OF ADENOSINE DEAMINASE GENES IN MAMMALIAN CELLS USING ADENOSINE, ALANOSINE, URIDINE, AND DEOXYCOFORMYCIN

[75] Inventors: Rodney E. Kellems; Cho-Yau Yeung, both of Houston, Tex.

[73] Assignee: Baylor College of Medicine, Houston, Tex.

[21] Appl. No.: 627,957

[22] Filed: Jul. 5, 1984

[51] Int. Cl.$^4$ .................... C12P 219/3.4; C12P 21/00; C12N 15/00
[52] U.S. Cl. ........................................ 435/91; 435/68; 435/70; 435/172.3; 435/317.1; 435/320; 935/62; 935/70; 536/27
[58] Field of Search ...................... 435/41, 68, 91, 226, 435/240, 241, 253; 935/62, 70, 71

[56] References Cited

U.S. PATENT DOCUMENTS 4,396,601 8/1983 Salser et al. .............................. 424/94
4,497,796 2/1985 Salser et al. .............................. 424/95

OTHER PUBLICATIONS

Lehninger, Principles of Biochemistry (1982) Worth Pub., N.Y., N.Y., pp. 215–216.
Chan et al. (1978) Somatic Celo Gen. 4: 1–12.
Hoffee et al. (1982) Somatic Cell Gen. 8: 465–477.
Yeung, C.-Y. et al., Jul. 1983, J.B.C. 258:8338.
Yeung, C.-Y. et al., Dec. 1983, J.B.C. 258:15179.
Yeung, C.-Y. et al., Jul. 1983, J.B.C. 258:8330.
Kaufman, R. et al., Apr. 1983, M.C.B. 3:699.

*Primary Examiner*—Thomas G. Wiseman
*Assistant Examiner*—S. Seidman
*Attorney, Agent, or Firm*—Fulbright & Jaworski

[57] ABSTRACT

Disclosed are cultured mouse cells with amplified adenosine deaminase genes which greatly overproduce adenosine deaminase. The cells were isolated by growth in media containing alanosine, uridine, and a cytotoxic concentration of adenosine. Maximum enhancement of adenosine deaminase activity was achieved by also adding deoxycoformycin to the media and then serially increasing the deoxycoformycin concentration at 4 to 6 week intervals. Also disclosed is a cDNA homologous to mouse adenosine deaminase mRNA. The cDNA was produced by synthesis against RNA extracted from the cells containing amplified adenosine deaminase genes and then inserted into a bacterial plasmid. Multiple copies of the cDNA were produced by replication of the bacteria into which the plasmids were inserted.

16 Claims, 5 Drawing Sheets

AMPLIFICATION OF ADENOSINE DEAMINASE GENES IN MAMMALIAN CELLS USING ADENOSINE, ALANOSINE, URIDINE, AND DEOXYCOFORMYCIN

BACKGROUND OF THE INVENTION

Adenosine deaminase is an enzyme of purine nucleoside metabolism that is present in varying levels in virtually all mammalian tissues. The highest adenosine deaminase levels are found in gastrointestinal tract tissues and lymphocytes and their associated organs such as the spleen and thymus. The adenosine deaminase expression level in the gastrointestinal tracts of mice increases dramatically following birth in apparent coordination with the change of diet that accompanies weaning. Lee, P. C., 31 Developmental Biology 227-33 (1973). The developing thymus and spleen of neonatal humans also express high levels of adenosine deaminase, possibly in coordination with the postnatal development of the immune system. Adams, A., and Harkness, R. A., 26 Clinical Experimental Immunology 647-49 (1976). These developmental features of adenosine deaminase gene expression suggest that the adenosine deaminase gene locus may serve as a model system for studying mammalian developmental gene regulation.

Abnormalities of adenosine deaminase gene expression are correlated consistently with human disease. Individuals lacking adenosine deaminase expression develop severe combined immunodeficiency disease, an autosomal recessive genetic disorder characterized by a lack of functional B- and T-lymphocytes. Pharmacologic studies have demonstrated that suppression of adenosine deaminase by specific inhibitors can lead to severe lymphopenia in humans and mice. Data which show that supplementing cultured lymphoblasts from adenosine deaminase deficient severe combined immunodeficiency disease patients with calf-derived adenosine deaminase restores the T-cell specific mitogen responsiveness and E-rosetting capabilities of these cells strongly suggests that adenosine deaminase gene expression is essential for proper T- and B-lymphocyte development in mammals. In contrast, a 45- to 70-fold increase in erythrocyte adenosine deaminase is associated with a dominantly inherited hemolytic anemia. Valentine, W. N., et. al., 195 Science 783-85 (1977); Fujii, H., et. al., 51 British Journal of Hematology 427-31 (1982).

The acquisition of adenosine deaminase antibodies and nucleic acid probes complementary to the adenosine deaminase gene sequences is essential for studying mammalian adenosine deaminase gene structure, regulation, and function. Adenosine deaminase is a low abundance protein; in cells that express this enzyme at the highest level, adenosine deaminase constitutes no more than 0.1% of total protein. Thus, the isolation of mutant cell lines with amplified adenosine deaminase genes which produce adenosine deaminase at greatly increased levels would facilitate the production of adenosine deaminase antibodies and nucleic acid probes complementary to the adenosine deaminase gene sequences. These cell lines would also provide a commercially attractive source of adenosine deaminase. Some previous successful attempts at isolating cell lines with amplified genes have relied upon the use of specific inhibitors of essential enzymes. Alt, F. W., et. al., 253 J. Biological Chemistry 1357-70 (1978); Wahl, G. M., 254 J. Biological Chemistry 8679-89 (1979). Other successful efforts have exploited the ability of specific enzymes or proteins to detoxify or sequester a cytotoxic compound. Beach, L. R., and Palmiter, R. D., 78 Proceedings National Academy Sciences U.S.A. 2110-14 (1981). A combination of these approaches was chosen to obtain cells capable of enhanced adenosine deaminase synthesis.

Adenosine deaminase gene expression is not required for growth of cells in culture. Therefore, isolating cell lines with amplified adenosine deaminase genes required the development of a selection system that prevented growth of cells lacking adenosine deaminase expression. A selection system termed 11AAU was developed by increasing the adenosine concentration of the adenosine kinase selection medium, AAU (adenosine, alanosine, uridine), 11-fold, a cytotoxic level. Yeung, C., et. al., *Selective Overproduction of Adenosine Deaminase in Cultured Mouse Cells*, 258 J. Biological Chemistry 8338-45 (1983); Yeung, C. Y., et. al., *Isolation of a Mouse Cell Line That Overproduces Adenosine Deaminase*, in *Intercellular Communication in Leukocyte Function*, John Wiley and Sons, New York (1983). 11AAU selected not only for the expression of adenosine kinase but also for that of adenosine deaminase which served to detoxify excess adenosine by converting it to inosine. Cultured mouse cells grown in media containing 11AAU in conjunction with a stepwise selection for resistance to increasing concentrations of deoxycoformycin, an adenosine deaminase inhibitor, produced highly drug-resistant cells with up to a 10,000-fold increase in adenosine deaminase activity. In these cells, adenosine deaminase accounts for over one-half of the soluble protein. This finding represents a dramatic improvement over the 20-fold adenosine deaminase increase obtained by other investigators using rat hepatoma cells in a substantially different selection medium. Hoffee, P. A., et. al., 8 Somatic Cell Genetics 465-77 (1982). The success of the presently invented selection system was recently reported by Fox in *Gene Amplification and Drug Resistance* 307 Nature 212, Jan. 19, (1984). It is anticipated that further studies growing cultured mouse cells in a medium containing 11AAU and increasing concentrations of deoxycoformycin will produce cells with even greater adenosine deaminase levels.

Studies designed to elucidate the molecular basis of the enhanced adenosine deaminase production observed in the cultured mouse cells grown in media containing 11AAU demonstrated that the mRNA level coding for adenosine deaminase was greatly elevated in these cells. Yeung, C. Y., et. al., *Amplification and Molecular Cloning of Murine Adenosine Deaminase Gene Sequences* 258 J. Biological Chemistry, 15179-85 (1983). Using total poly(A+)RNA derived from these cells as an enriched source of adenosine deaminase mRNA a cDNA library was constructed and cDNA clones containing sequences homologous to adenosine deaminase mRNA were isolated. RNA blot hybridization analysis indicated that three different poly(A+)RNA species which cross-hybridized with cloned adenosine deaminase cDNA sequences were greatly elevated in this cell line. One of the adenosine deaminase cDNA clones was used to demonstrate that the increased adenosine deaminase level in these cells could be fully accounted for by an increase in adenosine deaminase gene copy number.

In addition to their usefulness as a commercially attractive source of adenosine deaminase, the adenosine deaminase gene amplification mutant cells have proven to be a most effective approach towards cloning adenosine deaminase gene sequences. The nucleic acid probes available as a result of the isolation of these mutant cells provide the means to explore basic questions about adenosine deaminase mRNA and gene structure and to generate an adenosine deaminase expression vector potentially useful for adenosine deaminase gene replacement therapy. The presently invented mutant cell selection system and cloned adenosine deaminase genes are also useful in conjunction to co-amplify other mammalian genes for which no selectible phenotype is known. This is accomplished by attaching the adenosine deaminase gene to another gene of interest, introducing this recombinant DNA into cultured mammalian cells, and selecting for amplification of adenosine deaminase genes.

PRIOR ART STATEMENT

Applicants are unaware of any prior art teaching the 11AAU selection system or its use alone or in combination with deoxycoformycin in cultured cell systems to produce mutant cells with amplified adenosine deaminase genes capable of greatly enhanced adenosine deaminase production. Applicants are also unaware of any prior art teaching the isolation of cDNA clones containing sequences homologous to murine adenosine deaminase mRNA.

A preliminary report of the successful isolation of a mouse cell line that overproduces adenosine deaminase using the 11AAU selection system was published in abstract form by the applicants in November 1982. Yeung and Kellems, *Isolation of a Mouse Cell Line that Overproduces Adenosine Deaminase*, 163 Immunobiology 274 (Nov. 1982) (Copy attached). However, this abstract lacked sufficient detail to enable a reasonably skilled biochemist or immunologist to produce cells which overproduce adenosine deaminase using the 11AAU selection system. Specifically, the abstract gave no indication that adenosine in a cytotoxic concentration was necessary, that alanosine in a concentration sufficient to block de novo AMP synthesis was necessary, or that uridine in a concentration sufficient to alleviate the block in UMP biosynthesis caused by adenosine was needed. Additionally, the abstract gave no indication of a minimum effective concentration of deoxycoformycin. To determine the effective concentrations of adenosine, alanosine, uridine, and deoxycoformycin based on the limited information contained in the abstract would have required extensive additional experimentation and inventive effort. Thus, publication of this abstract does not bar the claims made in this application.

Prior art does teach a method of increasing the expression of an adenosine deaminase gene in cultured mammalian cells using adenine nucleosides. Yeung, C. Y., et. al., *Increased Expression of One of Two Adenosine Deaminase Alleles in a Human Choriocarcinoma Cell Line Following Selection With Adenine Nucleosides*, 258 J. Biological Chemistry 8330-37 (1983). However, in contrast to the present invention employing cultured mouse cells, a human choriocarcinoma cell line was used. Additionally, a different selection system containing cytotoxic adenosine analogues was used. Using this system, the maximum enhancement of adenosine deaminase gene expression was only 20-fold.

Examples of other amplified genes induced by selective pressure upon cultured cells are found in the prior art. The most significant of these involves exposing Chinese hamster ovary cells to increasing concentrations of methotrexate to amplify the dihydrofolate reductase gene sequences. This system has been used to co-amplify genes for certain desired products.

A selection system for isolating somatic cell hybrids containing adenosine kinase has been previously reported. Chan, T., et. al., *Adenosine Kinase As a New Selective Marker in Somatic Cell Genetics : Isolation of Adenosine Kinase-Deficient Mouse Cell Line and Human-Mouse Hybrid Cell Lines Containing Adenosine Kinase*, 4 Somatic Cell Genetics 1-12 (1978). This selection system employs adenosine, alanosine, and uridine as the selective agents. In contrast, the presently invented selection system selects for a different enzyme, adenosine deaminase; requires an 11-fold higher concentration of adenosine; and incorporates deoxycoformycin as an adenosine deaminase inhibitor.

SUMMARY OF THE INVENTION

The present invention is directed to cultured mouse cells with amplified adenosine deaminase genes which overproduce adenosine deaminase, a selection medium for producing and isolating these cells, methods of producing and isolating these cells employing this selection medium, cDNA homologous to murine adenosine deaminase mRNA, methods of producing the cDNA, and transformants containing cDNA homologous to the murine adenosine deaminase mRNA sequences.

Accordingly, it is an object of the present invention to provide cultured mouse cells with amplified adenosine deaminase genes which overproduce adenosine deaminase.

A further object of the present invention is to provide a selection medium capable of producing and isolating cultured mouse cells with amplified adenosine deaminase genes.

A further object of the present invention to is provide a method of producing and isolating these cultured mouse cells employing this selection medium.

Another object of this invention is to provide a cDNA homologous to adenosine deaminase mRNA.

Another object of this invention is to provide a method of producing cDNA homologous to adenosine deaminase mRNA.

A still further object of this invention is to provide transformants containing cDNA homologous to adenosine deaminase mRNA.

Other and further objects, features, and advantages appear throughout.

DESCRIPTION OF THE PREFERRED EMBODIMENTS

The following organisms are available from permanent collection of the American Type Culture Collection, 12301 Parklawn Drive, Rockville, Md. 20852, U.S.A.

ATCC CRL8588: Mouse C1-1D derived cell line B-1/100

ATCC 39755 : E.Coli pcAM-7-33

The deposits are available to the public upon a grant of a patent to the Assignee, Baylor College of Medicine, disclosing them. It should be understood, however, that the availability of a deposit does not constitute a license to practice the subject inventions in derogation of patent rights granted by governmental action.

PRODUCTION AND ISOLATION OF CULTURED MOUSE CELLS WITH AMPLIFIED ADENOSINE DEAMINASE GENES.

Materials

Alanosine was obtained from the Drug Synthesis and Chemistry branch and 2'-deoxycoformycin was obtained from the Natural Products Branch, Division of Cancer Treatment, National Cancer Institute.

Cell Lines and Culture Conditions

Mouse C1-1D, a thymidine kinase deficient mouse fibroblast cell line was used as the parental cell line. Cells were maintained in Dulbecco's modified Eagle's medium supplemented with 15% horse serum (Grand Island Biological Company) and incubated at 37° C. in a humidified atmosphere of 95% air and 5% CO2. Horse serum was used because it has very low levels of adenosine deaminase as compared with fetal Serum. All cell lines were tested periodically and found to be free of mycoplasma contamination.

The 11AAU selection medium used selects simultaneously for adenosine deaminase and adenosine kinase and consists of 1.1 mM adenosine, 50 µM alanosine, and 1 mM uridine in Dulbecco's modified Eagle's medium supplemented with 15% horse serum.

SIMULTANEOUS SELECTION FOR ADENOSINE DEAMINASE AND ADENOSINE KINASE: THE 11AAU SELECTION SYSTEM

To circumvent potential problems caused by the presence of adenosine kinase-deficient mutants, we developed a new protocol that selected simultaneously for adenosine deaminase and adenosine kinase. The new protocol is a modification of a selection system (termed AAU) designed to select for adenosine kinase. The modification involved an 11-fold increase in the adenosine concentration to 1.1 mM. The important components of the 11AAU medium are alanosine (0.05 mM) which serves to block de novo AMP synthesis, adenosine (1.1 mM) which provides a salvage route for AMP synthesis via the adenosine kinase reaction, and uridine (1.0 mM) which alleviates the block in UMP biosynthesis caused by adenosine at the concentration employed. Because adenosine is cytotoxic at a concentration of 1.1 mM adenosine deaminase is required to detoxify excess adenosine by converting it to inosine. Thus, cells that can survive 11AAU selection must not only be able to utilize the exogenous adenosine via adenosine kinase but must also be able to detoxify the excess adenosine via the unidirectional adenosine deaminase pathway.

Mouse C1-1D cells selected for resistance to 11AAU expressed adenosine deaminase at a level approximately 1.4-fold greater than that of parental C1-1D cells as determined by spectrophotometric assay. This level of adenosine deaminase expression presumably was essential for those cells to survive in 11AAU since suppression of cellular adenosine deaminase activity by 10 nM deoxycoformycin killed these cells in 11AAU selection medium. In the absence of 11AAU selection medium, adenosine deaminase expression was not required judging from the fact that cells were not killed by up to 50 µM deoxycoformycin.

The adenosine kinase expression of 11AAU-resistant cells was retained at a level approximately 40% that of parental C1-1D cells. Thus, resistance to 11AAU selection was associated with an increase in adenosine deaminase activity and a decrease in adenosine kinase activity.

SELECTION FOR INCREASED ADENOSINE DEAMINASE PRODUCTION USING INCREASING CONCENTRATIONS OF DEOXYCOFORMYCIN IN CONJUNCTION WITH 11AAU

Figure 1:
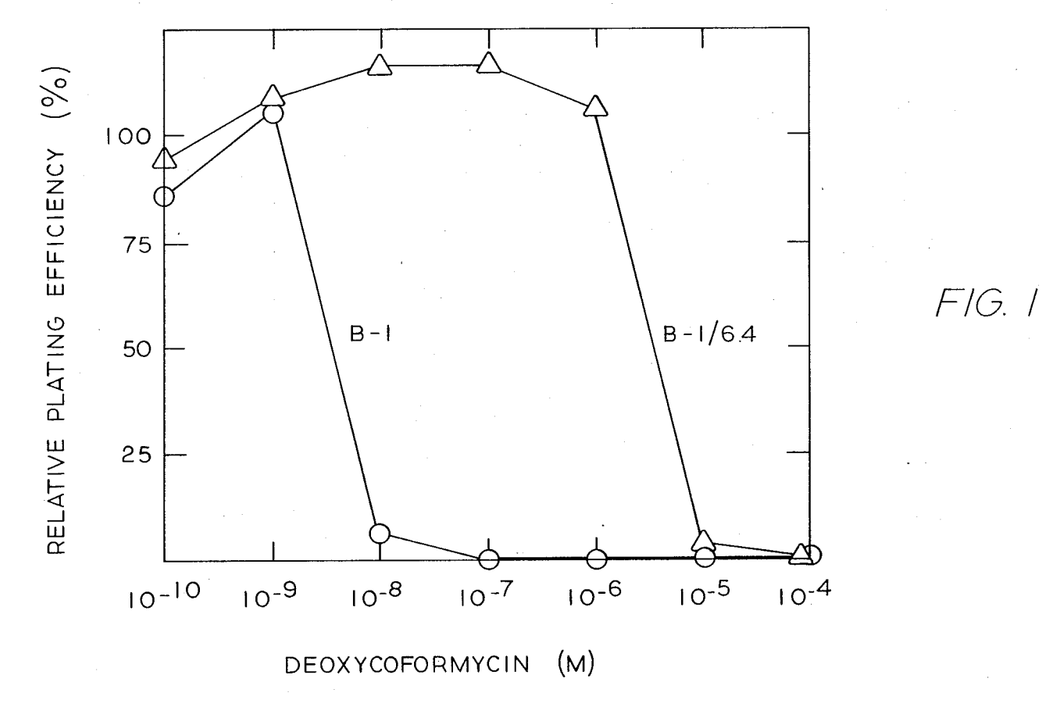
FIG. 1 is a graphic representation of the relative plating efficiencies of 11AAU-resistant (B-1) and 11AAU+6.4 $\mu$M deoxycoformycin-resistant (B-1/6.4) cells in 11AAU medium plus various concentrations of deoxycoformycin.
Figure 2:
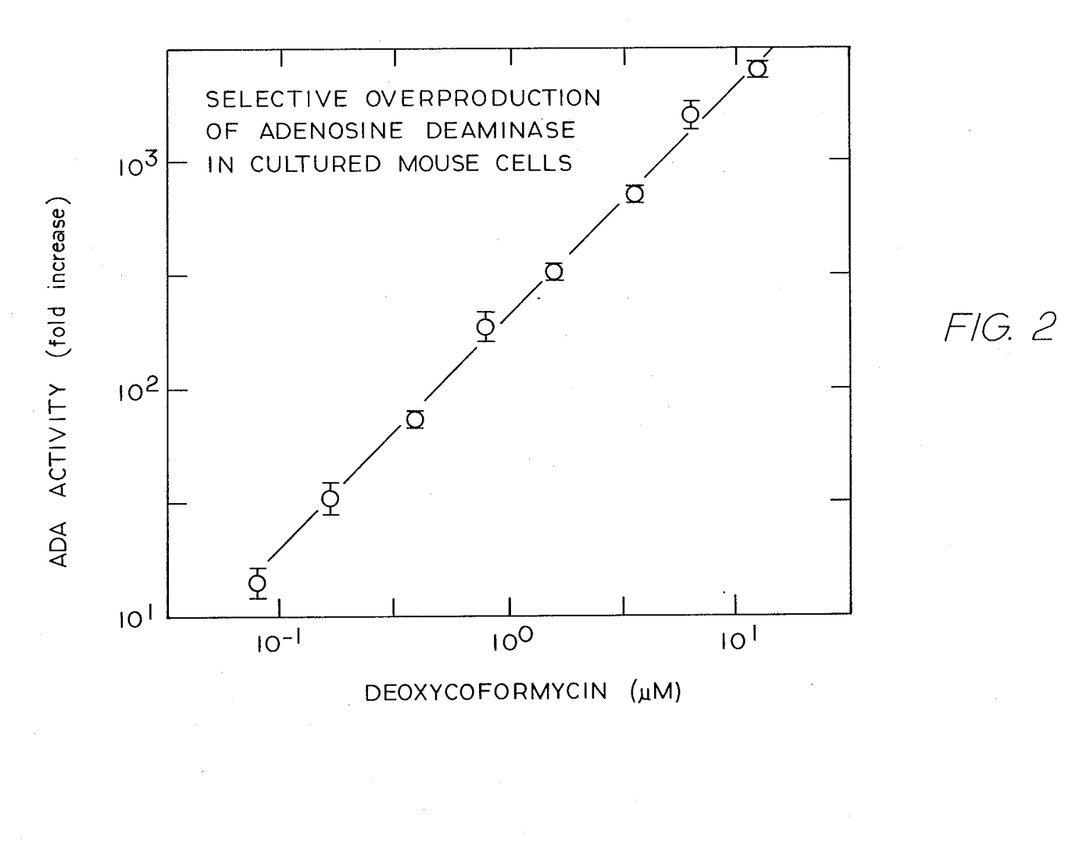
FIG. 2 is a graphic representation of the relationship between adenosine deaminase activity and deoxycoformycin resistance in 11AAU-resistant cells.

The level of adenosine deaminase required for growth in 11AAU was approximately 40% greater than that normally present in C1-1D cells. It was possible to isolate from 11AAU-resistant cells, those which were resistant to 11AAU plus increasing concentrations of deoxycoformycin, starting at a deoxycoformycin concentration of 10 nM. Selection pressure was increased at 4- to 6-week intervals by doubling the deoxycoformycin concentration used in conjunction with 11AAU medium. Continued selection in 11AAU for increasing deoxycoformycin resistance resulted in the isolation of highly drug-resistant cells as judged by the relative plating efficiencies in the presence of 11AAU and various concentrations of deoxycoformycin. (FIG. 1). The increased adenosine deaminase activity in the drug-resistant cells was linearly correlated with a level of deoxycoformycin resistance with a slope of exactly 1. (FIG. 2). This indicated that increased deoxycoformycin resistance was fully accounted for by a corresponding increase in cellular adenosine deaminase levels. Throughout the series, adenosine kinase expression remained relatively stable at a level approximately 40% that of parental C1-1D cells.

Electrophoretic analysis of proteins extracted from C1-1D cells and cells resistant to 11AAU plus increasing concentrations of deoxycoformycin indicated that the increased adenosine deaminase activity was accompanied by an increased abundance of a protein having an apparent molecular weight of 41,000 Daltons. This protein was not readily detectable in the parental cells but was the most abundant protein extracted from the deoxycoformycin resistant cells. In the most highly resistant cells, this protein accounted for approximately half the soluble protein. Histochemical staining following protein separation by isoelectric focusing demonstrated that the 41,000 Dalton protein comigrated with adenosine deaminase activity.

MOLECULAR CLONING OF MOUSE ADENOSINE DEAMINASE GENE SEQUENCES.

RNA Preparation

RNA was extracted from several grams of early to mid-log phase C1-1D mouse cells selected for resistance to 11AAU and deoxycoformycin. Cells were grown in roller bottles and received fresh media 3 to 5 hours before harvesting. Immediately prior to harvest, cells were rinsed twice with ice-cold Hanks' balanced salts solution, then scraped from roller bottles with a rubber policeman, and washed three additional times with Hanks' balanced salts solution. All subsequent operations were carried out at 0–4° C. Cell pellets were homogenized in 7 volumes of 25 mM Tris/Cl, pH 7.1, 25 mM NaCl, 10 mM $MgCl_2$, 5% (W/V) sucrose, and 1 mg. per ml. of heparin by five strokes with a Dounce homogenizer. One cell volume of 10% (v/v) Triton X-100, 10% (w/v) deoxycholate was added, and the homogenate was given five additional strokes. The homogenate was centrifuged for ten minutes at $27,000 \times g_{max}$ and to the supernatant was added 0.2 volume of 10% (w/v) sodium dodecyl sulfate, 50 mM EDTA, and 100 mM Tris/Cl, pH 7.1. After four or five successive phenol/chloroform extractions, the RNA was precipitated overnight in 0.4 M NaCl and 70% ethanol at $-20°$ C. The RNA was pelleted by centrifugation for 10 minutes at $18,000 \times g_{max}$ at 4° C., vacuum-dried for 15 minutes, and resuspended in a minimum volume of 1% (w/v) sodium dodecyl sulfate, 5 mM EDTA, and 10 mM Tris-HCl, pH 7.1. The resuspended RNA was then treated with 200 μg/ml of proteinase K at 37° C. for 30 minutes, re-extracted with phenol/chloroform twice and precipitated in 0.4 M NaCl and 70% ethanol overnight at $-20°$ C. The RNA was then pelleted by centrifugation for 10 minutes at $18,000 \times g_{max}$ at 4° C., resuspended in sterile water, and re-precipitated in 3 M sodium acetate buffer, pH 5.5, at 0° C. for two hours to remove any contaminating DNA. The RNA was then pelleted by a centrifugation as before and resuspended in sterile water. Poly(A+)RNA was isolated by one or two cycles of oligo(dT)-cellulose chromotography using KCl to precipitate the poly-(A+)RNA.

CONSTRUCTION OF RECOMBINANT PLASMIDS AND IDENTIFICATION OF CANDIDATE ADENOSINE DEAMINASE CDNA CLONES BY HYBRIDIZATION

With Prehybridized [$^{32}$p]cDNA

The first step in the production of adenosine deaminase cDNA clones was the construction of a cDNA library using poly(A+)RNA derived from the cell line which was resistant to 11AAU and deoxycoformycin. The following method was employed to construct the cDNA library:

(1) Poly(A+)RNAs derived from the resistant cell line were used as templates to synthesize the complementary DNAs.

(2) The complementary DNAs from (1) were then used to synthesize double-stranded cDNAs.

(3) Next, S1 nuclease was used to generate blunt-ended double-stranded cDNAs.

(4) Terminal deoxynucleotide transferase (TdT) was then used to add approximately 15 dCMP nucleotides to the 3' ends of the cDNAs.

(5) TdT was then used to add approximately 15 dGMP nucleotides to pBR322 vector that had been linearized using the restriction enzyme PstI.

(6) The "tailed" cDNAs from (4) were then annealed with the tailed vector in (5).

(7) The annealed vector:cDNAs were then used to transform E. coli strain RR1, selecting for $Tet^R$ and $Amp^S$ transformants.

Step (1) involved using aprpxoimately 100 μg of Poly(A+) RNA derived from resistant cells as a template, in a 1 ml reaction solution containing (50 mM Tris-HCl, pH 8.3; 50 mM KCl; 10 mM $MgCl_2$; 40 mM β-mercaptoethanol, 12 μg/ml oligo-$dT_{12-18}$; 40 μg/ml Actinomycin D; 1 mM dATP; 1 mM dGTP; 1 mM TTP; 280 Units AMV reverse transcriptase) to synthesize single-stranded cDNAs at 46° C. for 30 minutes. The cDNA-RNA complex was denatured and the RNA degraded in (0.1 N NaOH, 10 mM EDTA, 900 mM NaCl) for 1 hour at 20° C. The cDNAs were then fractionated over a 5–25 percent sucrose gradient in 0.1 N NaOH, 0.9 M NaCl and 1 mM EDTA by centrifugation for 20 hours using an SW50.1 rotor at 40,000 rpm. The first peak fraction of the gradient was pooled and the DNAs recovered by ethanol precipitation were used for 2nd strand cDNA synthesis.

Step (2) involved using the single-stranded cDNAs from (1) as templated to synthesize double-stranded cDNAs in a 100 μl solution containing (50 mM Tris-HCl, pH 8.3; 10 mM $MgCl_2$; 40 mM β-mercaptoethanol; 1 mM dGTP; 1 mM dCTP; 1 mM dATP; 1 mM dTTP; 60 U AMV reverse transcriptase). After incubation at 46° C. for 90 minutes, the reaction was terminated by addition of 25 μl of 0.1 M EDTA. The double-stranded cDNAs were chromatographed over an Ultrogel ACA54 column and the DNA recovered by ethanol precipitation.

Step (3) involved treating the double-stranded cDNAs from (2) with 1000 Units of S1 nuclease in a 200 μl reaction mixture containing 30 mM sodium acetate, pH 4.5; 280 mM NaCl; 45 mM Zn acetate). After incubation for 60 minutes at 20° C., the cDNAs were treated with 20 μl of 1 M Tris-base and 0.1 M. EDTA, extracted in phenol, chromatographed over an Ultrogel ACA54 column and precipitated in ethanol.

Step (4) involved treating the blunt-ended cDNAs derived from (3) with 75 Units of terminal deoxynucleotide transferase in a 250 μl solution containing (200 mM potassium cacodylate, pH 72.; 1 mM $CaCl_2$; 1 mM β-mercaptoethanol; and 5 μM dCTP) at 37° C. for approximately 7 minutes. The "tailed" cDNA was chromatographed over an Ultrogel ACA54 column and recovered by ethanol precipitation.

Step (5) involved treating 50 μg of PstI digested pBR322 vector with 150 units of terminal deoxynucleotide transferase in a 510 μl solution containing (200 mM potassium cacodylate, pH 7.2; 1 mM $CaCl_2$; 1 mM β-mercaptoethanol; and 5 μM dGTP) for approximately 10 minutes at 37° C. The "tailed" vector was chromatographed over an Ultrogel ACA54 column and recovered by ethanol precipitation.

Step (6) involved putting equal-molar amounts of "tailed" cDNA from (4) and "tailed" vector from (5) in a 400 μl solution containing (10 mM Tris-HCl, pH 7.6; 100 mM NaCl; 1 mM EDTA). The concentration of vector used was 2 μg/ml. The mixture was heated at 68° C. for 30 minutes, incubated at 42° C. for 3 hours and slow cooled to 20° C. overnight.

Step (7) involved adding 100 μl of the reannealed vector-cDNA from (6) to approximately 5×10⁹ transformation competent (ref. Manel, M. and Higa, A. :J. Mol. Biol. 53:154, 1970) and incubate in ice for 30 minutes. The cells were then heat shocked at 42° C. for 2 minutes. Then add 20 mL of L-broth to the cells and incubate at 37° C. for 1 hour. The cells were then precipitated by centrifugation, resuspended in 5 ml of L-broth and plated onto L-broth plates containing 12.5 μg/ml Tetracycline. Recombinant colonies showed up after overnight incubation at 37° C.

The cDNA library was then screened by hybridization with prehybridized [$^{32}$P]-labeled cDNA synthesized from total poly(A+)RNA derived from the resistant cells to determine which of the recombinant colonies contained adenosine deaminase genes. The prehybridized [$^{32}$P]-labeled cDNA was prepared by the following method:

(1) $^{32}$P-labeled cDNA complementary to total mRNA was synthesized by putting 5 μg of poly(A+)-RNA into a reaction mixture containing 50 mM Tris-HCl, pH 8.3; 50 mM KCl; 10 mM MgCl$_2$; 40 mM β-mercaptoethanol; 12 μg/ml oligo dT$_{12-18}$; 40 μg/ml Actinomycin D; 1 mM dATP; 1 dGTP; 1 mM dTTP; 250 μCi α-[$^{32}$P]dCTP (approximately 70 μCi/mM) ; 50 Units AMV reverse transcriptase in a 100 μl solution and incubating at 46° C. for 30 minutes. Then 25 μl of 1 N NaOH was added to the reaction mixture and the entire mixture was allowed to stand at room temperature (20° C.) for 1 hour to degrade the RNA. The reaction mixture was then passed over an Ultrogel ACA54 column to remove the unincorporated label. The [$^{32}$P]-labeled cDNA was pooled and precipitated using ethanol at −20° C. with yeast tRNA as carriers.

(2) Preparation of [$^{32}$P]-labeled cDNA which can hybridize specifically with amplified mRNA:

The [$^{32}$P]-labeled cDNA synthesized in (1) was precipitated by centrifugation. The supernatant was removed, and the precipitated cDNA was dried for 15 minutes under vacuum. The dried down cDNA was then resuspended in 500 μl of sterile 1X Denhardt solution containing 0.9 M NaCl; 20 mM Tris-HCl, pH 7.5. 7.5 mg of total RNA derived from the parental C1-1D was added to this solution and the entire mixture was incubated at 68° C. overnight to remove by prehybridization non-amplified mRNA sequences.

This prehybridized [$^{32}$P]-cDNA was then used to screen the cDNA library. Approximately 20 percent of the recombinant colonies scored positive under these hybridization conditions. Several candidate recombinate clones were selected for further analysis to isolate adenosine deaminase clones.

IDENTIFICATION OF PROBABLE ADENOSINE DEAMINASE CLONES BY BLOT HYBRIDIZATION ANALYSIS

Candidate recombinant clones were further analyzed by RNA blot hybridization to see if the inserted cDNA sequences were homologous to an amplified poly(A+) RNA species found in the resistant cells. Plasmid DNAs isolated from these colonies were [$^{32}$P]-labeled by nick translation and used to probe RNA blots analyzing total poly(A+)RNA of parental and resistant cells. One specific clone, pADA600, containing a 600-base pair insert hybridized to all three (5.2, 1.7, and 1.5 kb) amplified poly(A+)RNA species present in the resistant cells. Seven additional clones with insert sizes ranging from approximately 340 to over 1,000 base pairs were identified on the basis of cross-hybridization to pADA600 under stringent hybridization and wash conditions. The DNA inserts within all eight clones contained a HindIII restriction endonuclease cleavage site approximately 200 base pairs from one of the two PstI sites flanking the inserted DNA sequences.

POSITIVE IDENTIFICATION OF THE pADA600 CLONE BY HYBRIDIZATION SELECTION

Figure 3:
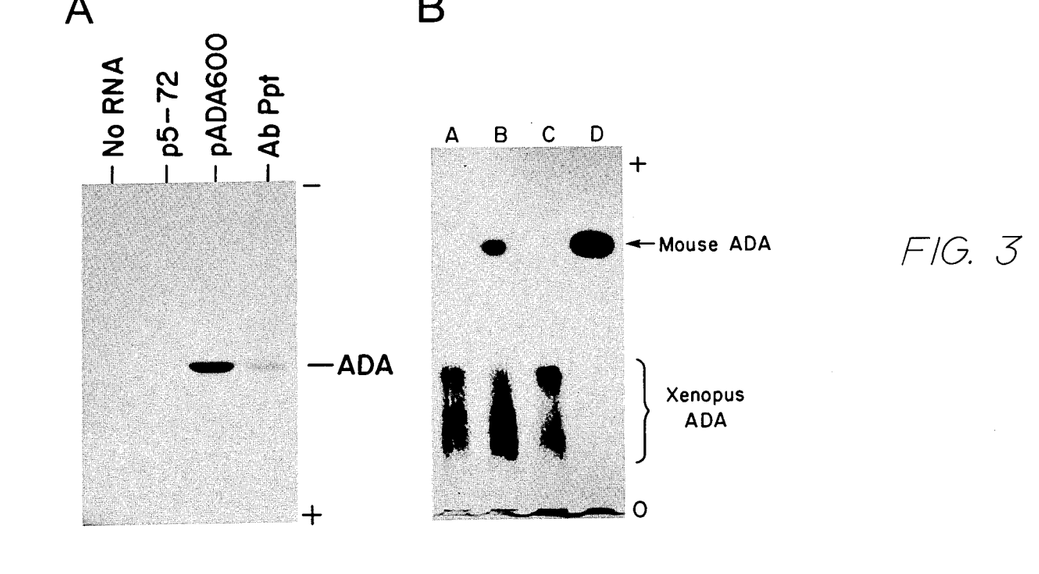
FIG. 3 is an analysis of translation products synthesized in the presence of hybridization-selected mRNA using rabbit reticulocyte lysate (A) and Xenopus oocyte (B) translation systems.

The DNA of clone pADA600 was denatured and immobilized on nitrocellulose filters. The immobilized DNA was allowed to hybridize with resistant cell-derived total poly(A+)RNA. RNAs eluted from the filter were translated in vitro using rabbit reticulocyte lysate and in vivo following mico injection into Xenopus oocytes. The results of the reticulocyte lysate assay indicate that RNA which was isolated by hybridization to pADA600 was able to program the synthesis of immunoprecipitable adenosine deaminase. (FIG. 3). Another cloned recombinant plasmid, p5–72, found in the cDNA library did not cross-hybridize with pADA600. RNA that was hybridization-selected against this control plasmid did not direct the synthesis of any detectable adenosine deaminase protein. These data provide strong evidence that the plasmid clone pADA600 contained inserted DNA sequences homologous to mouse adenosine deaminase mRNA.

Additional proof that pADA600 contained mouse adenosine deaminase mRNA sequences was provided by the translation of hybridization-selected mRNA using the Xenopus oocyte translation system. The plasmid clone pADA600 was clearly able to select by hybridization mRNA that directed the synthesis of enzymatically active mouse adenosine deaminase whereas a non-cross-hybridizing clone (P5–72) was not able to do so. Thus, pADA600 must have inserted DNA sequences complimentary to mouse adenosine deaminase mRNA.

ANALYSIS OF GENOMIC DNA BY BLOT HYBRIDIZATION

This experiment was conducted to determine if specific transcribed genomic DNA sequences were amplified in the adenosine deaminase overproducer cells. Genomic DNA was isolated as follows: Whole cells or nuclei were resuspended in 10 volumes of a balanced isotonic salt solution containing 0.5% sodium dodecyl sulphate and 250 μg/ml of proteinase K and incubated at 37° C. for at least eight hours. After phenol/chloroform extraction, the DNA was precipitated in 0.4 M NaCl and 70% ethanol overnight at −20° C. The DNA was then pelleted by centrifugation for 10 minutes at 18,000×g$_{max}$ at 4° C. and resuspended in water. The solution was made 1×SSC (0.15 M NaCl 0.015 M sodium citrate, pH 7) and treated with 50 μg/ml of ribonuclease A for 60 minutes at 37° C., followed by proteinase K (115 μg per ml) treatment for two hours at the same temperature. After another round of phenol/chloroform extraction, ethanol precipitation, and centrifugation as before, the DNA was resuspended in water and dialized overnight against water mixed with Chelex 100 and mixed-bed resin to remove any metallic ions. The DNA was digested with the restriction enzyme EcoRI and then electrophoresed in 0.8% agaros gel at 2.5 V/cm in TE buffer (40 mM Tris acetate, 1 mM EDTA, pH 8.2) for 16 hours. The DNA fragments were then blot-transferred to nitrocellulose paper according to the method of Southern. 98 J. Mol. Biol.

503-17 (1975). The blots were then hybridized with either [$^{32}$P]-labeled prehybridized cDNA or nick-translated [$^{32}$P]-labeled recombinant plasmids. The filters were washed extensively before autoradiography.

Figure 4:
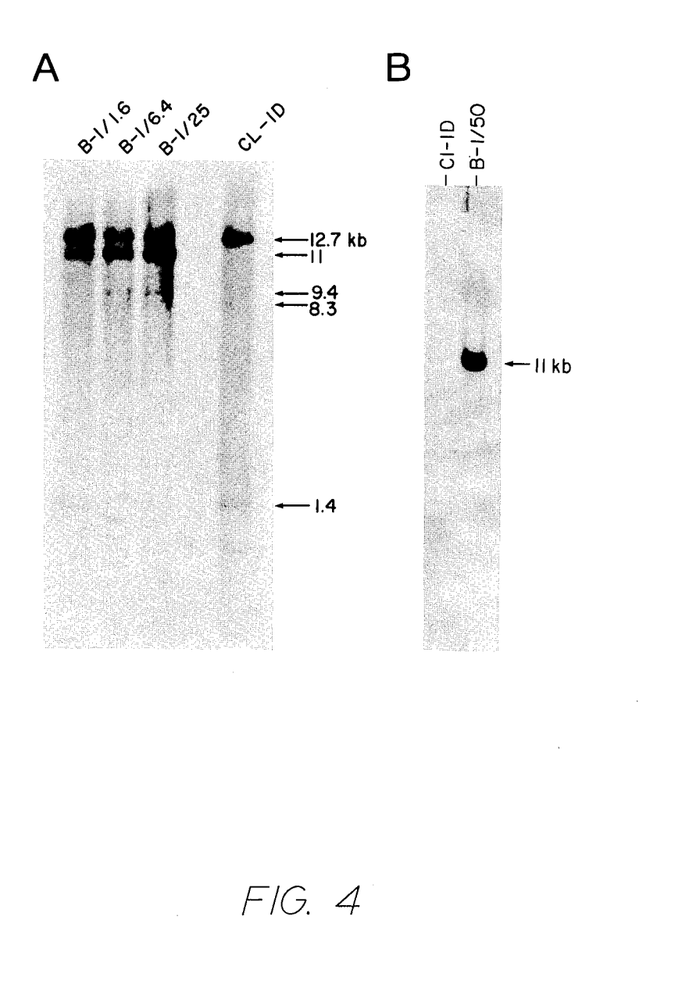
FIG. 4 is a blot hybridization analysis of genomic DNA from parental and drug-resistant cell lines using prehybridized $^{32}$P-labelled cDNA (A) and $^{32}$P-labelled pADA600 (B) as probes.

After digestion with the restriction enzyme EcoRI, genomic DNA of parental C1-1D cells and 11AAU and deoxycoformycin resistant cells was fractionated by agorose gel electrophoresis, blotted onto nitrocellulous paper, and probed with the prehybridized cDNA probe. The results showed that at least three EcoRI restricted DNA fragments (11, 9.4, and 8.3 kb in length) were amplified in the drug resistant line in apparent coordination with increased adenosine mRNA production in these cells (FIG. 4). The prehybridized [$^{32}$P]-labeled cDNA also hybridized to DNA fragments of 1.4 and 12.7 kb present at high copy number in both the parental and drug-resistant cells. When a similar blot containing only C1-1D and drug-resistant cell genomic DNA was probed with nick-translated pADA600 (or the larger adenosine deaminase clone, p13-108) only the 11-kb EcoRI restriction fragment hybridized with the probe. This showed that an 11-kb fragment contained adenosine deaminase gene sequences and was specifically amplified in the drug-resistant cells. In addition, the pADA600 plasmid does not contain the repeated sequences located in the 1.4 and 12.7-kb fragments. This suggested that the pADA600 probe could be used to quantitate the adenosine deaminase gene copy number in the drug-resistant cells.

ADENOSINE DEAMINASE GENE DOSAGE QUANTITATION USING DOT BLOT HYBRIDIZATION

DNA and RNA dot blot analyses were performed according to standard procedures using a Schleicher & Schuell minifold filtration manifold SRC-96 apparatus. Kafatos, F.C. et al., 7 Nucleic Acids Res. 1541-52 (1979). Nick-translated, [$^{32}$P]-labeled pADA600 plasmid was used as probe. Hybridization was performed in a solution containing 50% formamide, 6×SSC, 100 μg/ml of sheared single-stranded salmon sperm DNA, and 1×Denhardt's solution at 42° C. for 16 hours. Four hours after the initiation of hybridization, the probe was withdrawn and denatured again by heating at 72° C. for 15 minutes then added back to the nitrocellulose filter blot. The blots were extensively washed before autoradiography.

Figure 5:
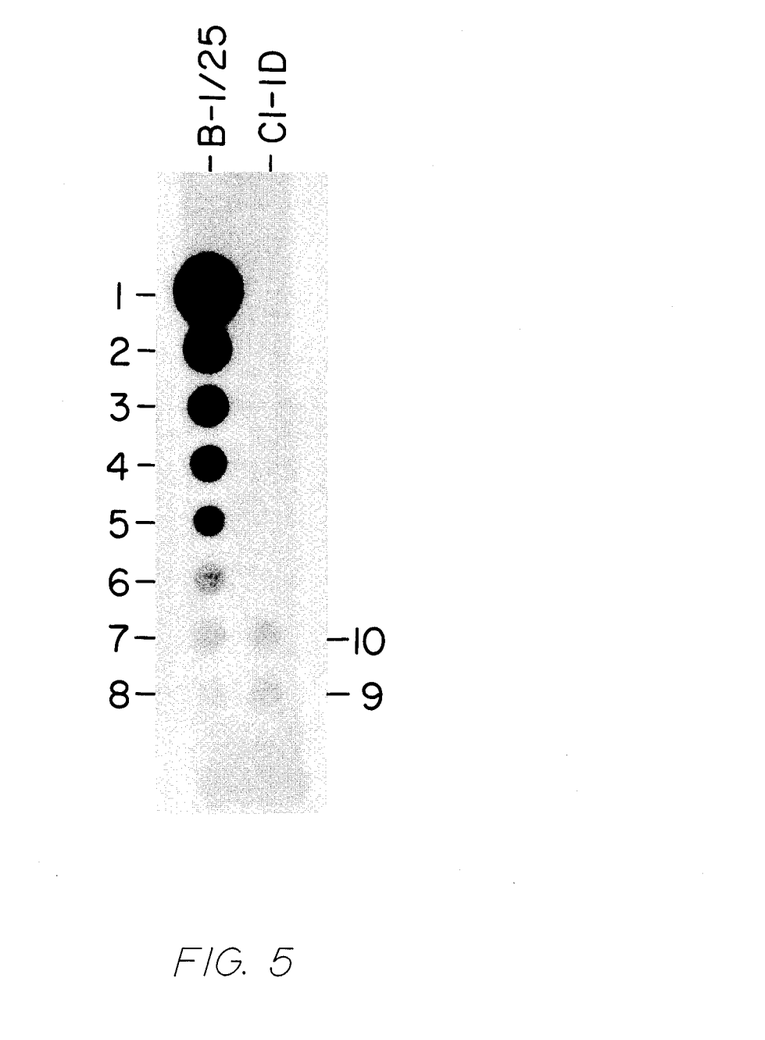
FIG. 5 is a dot blot hybridization to quantitate the fold amplification of the adenosine deaminase gene in the drug resistant cells (B-1/25).

Since the adenosine deaminase clone, pADA600, was found to hybridize with only a single EcoRI restricted genomic DNA fragment in the drug-resistant cells and showed no cross-hybridization with any repeated DNA sequences found in the parent C1-1D cells, we used this probe to quantitate the number of the adenosine deaminase gene copies in the drug-resistant cells as compared to the parent C1-1D cells. Dot blot hybridization using [$^{32}$P]-labeled pADA600 as probe showed that the tested cells contained approximately 2600-fold more adenosine deaminase gene copies than the C11D cells. (FIG. 5). This correlated quite closely with the 3200-fold increase in adenosine deaminase level in these drug-resistant cells as compared to the parental C1-1D cells.

The present invention, therefore, is well suited and adapted to obtain the objects and ends and has the advantages mentioned as well as others inherent therein.

What is claimed is:

1. A method for selects cultured mammalian cells with enhanced adenosine deaminase activity comprising:

growing the cells in a medium containing alanosine in a concentration sufficient to block de novo AMP synthesis, uridine in a concentration sufficient to alleviate the block in UMP biosynthesis caused by adenosine, and a cytotoxic concentration of adenosine.

2. Culture mammilian cells, produced by the method of claim 1, having an increased number of adenosene deaminase genes, wherein said cells produce elevated levels of adenosene deaminase when compared to the parental cells, said parental cells having at least one adenosene deaminase gene.

3. The cultured mammalian cells of claim 2 wherein the cells are mouse cells.

4. The cultured mammalian cells of claim 3 wherein the parental cells are from the mouse C1-1D fibroblast cell line.

5. The cultured mammalian cells of claim 4 having the deposit accession number ATCC CRL 8588.

6. A growth medium for cultured mammalian cells which selects cells with enhanced adenosine deaminase activity comprising:
    (a) adenosine in a cytotoxic concentration;
    (b) alanosine in a concentration sufficient to block de novo AMP synthesis; and
    (c) uridine in a concentration sufficient to alleviate the block in UMP biosynthesis caused by adenosine.

7. The growth medium of claim 6 wherein the concentration of adenosine is 1.1 mM.

8. The growth medium of claim 7 wherein the alanosine concentration is 0.05 mM.

9. The growth medium of claim 8 wherein the uridine concentration is 1.0 mM.

10. A growth medium for cultured mammalian cells which selects cells with enhanced adenosine deaminase activity comprising:
    (a) adenosine in a cytotoxic concentration;
    (b) alanosine in a concentration sufficient to block de novo AMP synthesis;
    (c) uridine in a concentration sufficient to alleviate the block in UMP biosynthesis caused by adenosine; and
    (d) deoxycoformycin in a concentration sufficient to inhibit less than all adenosine deaminase activity.

11. The growth medium of claim 10 wherein the adenosine concentration is 1.1 mM.

12. The growth medium of claim 11 wherein the alanosine concentration is 0.05 mM.

13. The growth medium of claim 12 wherein the uridine concentration is 1.0 mM.

14. The growth medium of claim 13 wherein the deoxycoformycin concentration is not less than 10 nM.

15. A method for isolating cultured mammalian cells with enhanced adenosine deaminase activity comprising:

growing the cells in a growth medium containing alanosine in a concentration sufficient to block de novo AMP synthesis, uridine in a concentration sufficient to alleviate the block in UMP biosynthesis caused by adenosine, adenosine in a cytotoxic concentration, and deoxycoformycin in a concentration sufficient to inhibit less than all adenosine deaminase activity.

16. The method of claim 15 wherein the adenosine deaminase activity of the cells is further enhanced by using an initial 10 nM deoxycoformycin concentration in the growth medium and then serially doubling the deoxycoformycin concentration at 4 to 6-week intervals.

* * * * *

UNITED STATES PATENT OFFICE
CERTIFICATE OF CORRECTION

Patent No. 4,822,736    Dated April 18, 1989

Inventor(s) Rodney E. Kellems and Cho-Yau Yeung

It is certified that error appears in the above-identified patent and that said Letters Patent is hereby corrected as shown below:

Column 2, line 41, change "Resistance307" to --Resistance, 307 --
Column 7, line 2, after "SEQUENCES" delete -- . --
Column 7, line 52, change "[$^{32}$p]" to -- [$^{32}$P] --
Column 8, line 9, change "aprpxoimately" to -- approximately --
Column 8, line 43, change "M. EDTA" to -- M EDTA --
Column 9, line 3, change "A. :J." to -- A. J. --
Column 9, line 24, change "1dGTP" to --1 mMdGTP --
Column 10, line 15, change "mico" to -- micro --
Column 10, line 49, change "phenol/_" to -- phenol/ --
Column 10, line 58, change "phenol/_" to -- phenol/ --
Column 11, line 64, change "selects" to -- selecting --
Column 12, line 5, change "Culture" to -- Cultured --
Column 12, line 5, change "mammilian" to -- mammalian --
Column 12, lines 6, 8 and 10, change "adenosene" to
-- adenosine --

Signed and Sealed this

Sixteenth Day of January, 1990

Attest:

JEFFREY M. SAMUELS

Attesting Officer    Acting Commissioner of Patents and Trademarks